United States Patent [19]
Penny

[11] Patent Number: 6,004,186
[45] Date of Patent: Dec. 21, 1999

[54] APPARATUS FOR SECURING SUCTION DEVICES TO A NURSING MOTHER'S BREASTS

[76] Inventor: Gretchen M. Penny, 5622 Merrimac Ave., Dallas, Tex. 75206

[21] Appl. No.: 08/884,609

[22] Filed: Jun. 30, 1998

[51] Int. Cl.[6] ................... A41D 1/20; A41C 3/04
[52] U.S. Cl. .................................... 450/36; 2/104
[58] Field of Search ................ 450/104, 56, 57, 450/37, 38; 2/104, 67, 106, 109; 604/74; D2/828, 840, 706, 708, 711, 731, 737, 793

[56] References Cited

U.S. PATENT DOCUMENTS

| | | |
|---|---|---|
| D. 137,782 | 4/1944 | Leser . |
| D. 170,509 | 9/1953 | Peck . |
| D. 321,273 | 11/1991 | Hull . |
| D. 366,351 | 1/1996 | Winchell . |
| 612,413 | 4/1898 | Murray . |
| 1,136,727 | 4/1915 | Smith . |
| 2,298,361 | 10/1942 | Freund . |
| 2,485,313 | 10/1949 | Rabinowitz . |
| 2,498,487 | 2/1950 | Elias . |
| 2,679,048 | 5/1954 | Alberts . |
| 3,306,299 | 2/1967 | Paramore . |
| 4,355,641 | 10/1982 | Dastoli et al. . |
| 4,390,024 | 6/1983 | Williams . |
| 4,550,734 | 11/1985 | Porco . |
| 4,633,876 | 1/1987 | Scullin . |
| 4,640,287 | 2/1987 | Anderson et al. . |
| 4,911,677 | 3/1990 | White . |
| 5,032,104 | 7/1991 | Rainville . |
| 5,092,812 | 3/1992 | Babcock . |
| 5,514,166 | 5/1996 | Silver et al. ........................ 604/74 |
| 5,575,768 | 11/1996 | Lockridge et al. . |
| 5,664,257 | 9/1997 | Hall . |

*Primary Examiner*—John J. Calvert
*Assistant Examiner*—Shirra L. Jenkins
*Attorney, Agent, or Firm*—Jenkens & Gilchrist

[57] ABSTRACT

An apparatus for securing the milk intake components of a suction device to the nipples of a nursing mother's breasts is configured as a bandeau or tube top. Alternatively, the apparatus may be configured as a halter top. The apparatus includes a chest piece for positioning around a nursing mother's chest and two openings formed in the front of the chest piece for receiving the milk intake components of the suction device. Optional closures such as Velcro® strips, snaps, hooks and eyes or buttons/button holes located on the chest piece permit adjusting the fit of the apparatus around the mother's chest. The halter top configuration may include a neck strap for adjusting the fit around the nursing mother's neck. Optional closures located on the neck strap permit adjusting the fit of the neck strap around the nursing mother's neck.

20 Claims, 6 Drawing Sheets

FIG. 2

FIG. 3 (FRONT VIEW)

FIG. 4 (SIDE VIEW)

FIG. 5 (REAR VIEW)

FIG. 6 (FRONT VIEW)

FIG. 7 (SIDE VIEW)

FIG. 8 (REAR VIEW)

FIG. 9 (REAR VIEW)

APPARATUS FOR SECURING SUCTION DEVICES TO A NURSING MOTHER'S BREASTS

BACKGROUND OF THE INVENTION

1. Technical Field of the Invention

This invention relates generally to apparatus for extracting breast milk, and more particularly, to an apparatus for securing suction devices to a nursing mother's breasts.

2. Description of Related Art

For many years, new mothers have elected to breast-feed their babies. Over the last decade, there has been a trend of more mothers selecting this feeding method. A growing number of employers are offering support to working mothers who continue to breast-feed their babies after returning from maternity leave. An integral part of the support offered by these companies is the opportunity for the women to extract breast milk while at work, either in the employee's office or in a special room or facility set aside for this purpose.

Mothers who wish to extract breast milk for later use by their infants have several options. Some mothers use electric, battery or manual breast pumps manufactured by companies such as Medela, Inc. Typically, a breast pump has a suction device that is secured to the nipple(s) of the mother's breast(s). Tubes connect to the suction device and to the breast pump, which creates a suction on the breast(s) to extract the breast milk. The suction device must be secured continuously and firmly to the breast(s) during the extraction procedure.

A mother may also use the breast pump and attachments to extract breast milk from both breasts simultaneously. A nursing mother may not wear any clothing on her upper body during the milk extraction procedure. Alternatively, if she is wearing a nursing brassiere, the mother may lower or remove the shield or flap portion of the nursing brassiere to expose the nipple(s) of her breast(s). Thereafter, she places the suction devices connected to the breast pump over the nipple(s) of her breast(s) and manually holds the suction devices firmly thereto throughout the procedure.

Various garments are available to assist new mothers in extracting breast milk using a breast pump. For example, U.S. Pat. No. 5,514,166 (the "'166 Patent") describes a nursing brassiere. Various attachments, such as slings, buttons, etc. are added to the nursing brassiere to hold the breast shields of the nursing brassiere in place against the mother's nipples.

The inventor distinguishes between a breast shield and a suction device. As used herein, breast shield refers to a fabric flap manufactured as part of, or permanently secured to, a nursing brassiere. Alternatively, a breast shield may be removably secured to the nursing brassiere. The breast shield may be lowered or removed to expose the breast for breast-feeding a baby or for milk extraction using mechanical means such as a breast pump. Breast shield may also refer to a removable, fabric pad placed inside the nursing brassiere that may help prevent milk leakage from the mother's breasts before and/or after the milk extraction procedure. These removable breast shields are usually disposed of on a routine basis after use. Breast shields are relatively inexpensive to purchase. During use, a breast shield lies over, or rests upon, a significant portion of the breast.

In contrast, a suction device is a removable, non-fabric apparatus that is used only during mechanical milk extraction, rather than during breast-feeding of a baby. The suction device includes various components, such as a milk intake component, various cylinders and caps. A suction device is not connected to a nursing brassiere, either temporarily or permanently. The milk intake component of the suction device is secured firmly and tightly to a nursing mother's nipples. The milk intake component covers a limited portion of the mother's breast, specifically the nipples and surrounding area. The other components of the suction device, such as the cylinders and caps are integrally connected to the milk intake component and have no physical contact with the mother's breasts.

While prior art garments may be suitable for some mothers, they have certain disadvantages. For example, breast milk extraction using a breast pump can be extremely time-consuming, e.g., thirty minutes per session. This is particularly common if the mother is using a breast pump that is limited to extracting milk from one breast at a time. Moreover, newborn babies often need to be fed eight to twelve times per day. Therefore, new mothers must extract breast milk many times a day in order to have an adequate supply of milk for their growing infants and to relieve the pressure in the mothers' breasts caused by a build-up of milk.

In addition, a mother must physically hold or otherwise secure the suction device to her breast(s). She may use one hand to hold the suction device in place and have one available hand if the breast pump uses only one suction device. However, it is difficult to do many tasks with only one hand. If a mother is using a breast pump with two suction devices, she is able to extract the breast milk twice as fast, but neither hand is available during the extraction procedure. As a result, the mother is effectively prevented from conducting any other activity during every milk extraction session. Depending on the number of times per day that a mother extracts milk, she may spend several hours each day connected to the suction devices of a breast pump and be unable to do anything else.

This is a major disadvantage for mothers who wish to extract breast milk from both breasts while simultaneously undertaking other activities, such as reading, writing, placing or receiving telephone calls, eating, etc. Moreover, working mothers who continue to extract breast milk for their babies are completely prevented from undertaking work activities several times per day. It is unrealistic to expect that working mothers will continue to follow a milk extraction regime if the mothers must spend one to two hours per day in this activity and very little can be accomplished during that time, not even a telephone call.

Often, breast pumps and their attachments do not provide adequate coverage to the breast area during the milk extraction procedure. Mothers, particularly those who work, are sometimes interrupted while extracting breast milk. Both the mother and the interrupting person may be embarrassed by the exposure of the mother's chest area.

Another disadvantage of the prior art apparatus is the cost. A mother typically uses a breast pump and related attachments for a short period of time, e.g. six to twelve months. Many of the breast pump aids, including garments such as nursing brassieres, are rather expensive. The purchase price of these devices may be prohibitive considering the relatively short time period during which a mother will be extracting milk from her breasts.

The apparatus of the '166 Patent also has numerous disadvantages. For example, the device uses numerous complicated attachments to hold the breast pump attachments to each breast. Specifically, the apparatus of the '166 Patent requires fasteners to be added to the suction devices and/or the nursing brassiere, or a harness-type strap arrangement for holding the breast shields against the breasts. The '166 Patent also discloses flaps to be attached to the nursing brassiere. However, the flaps permanently alter the nursing brassiere, so that it may no longer be suitable for breast-feeding.

Thus, there is a need for an apparatus for securing suction devices to a nursing mother's breasts that overcomes the disadvantages of prior art apparatus.

SUMMARY OF THE INVENTION

An apparatus for securing two milk intake components of a suction device to the nipples of a nursing mother's breasts comprises a chest piece for placement around a nursing mother's chest and two openings formed in the chest piece for receiving the milk intake components therethrough.

An alternative embodiment of the apparatus for securing two milk intake components of a suction device to the nipples of a nursing mother's breasts comprises a chest piece for placement around a nursing mother's chest; two openings formed in the chest piece for receiving the milk intake components therethrough; and a neck strap secured to the chest piece.

BRIEF DESCRIPTION OF THE DRAWINGS

For a more complete understanding of the present invention and the advantages thereof, reference is now made to the following Detailed Description of the Invention, taken in conjunction with the accompanying Drawings in which.

DETAILED DESCRIPTION OF THE INVENTION

Referring now to the drawings wherein like reference characters designate like or similar parts throughout the thirteen views, FIGS. 1, 3, 4, 5, 10, 11, 12 and 13 are various views of the apparatus of the present invention configured as a halter top 10. In the alternative, the apparatus may be configured as a bandeau or tube top (see FIGS. 2, 6, 7, 8 and 9).

Figure 9:
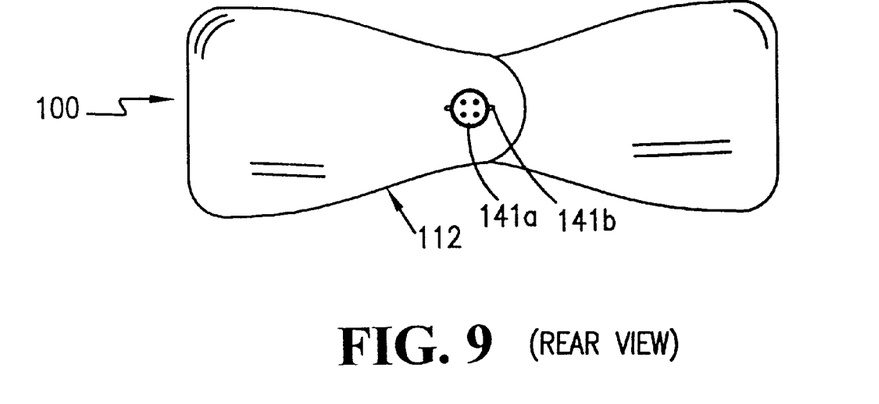
FIG. 9 is a rear view of the apparatus of FIG. 2, showing button/button hole closures on the ends of the chest piece.

The apparatus of the present invention configured as a halter top 10 includes several components. The chest piece 12 is the primary component of the apparatus 10. The chest piece 12 may be manufactured as a single strip of fabric having an essentially constant width along the entire chest piece 12 (see FIG. 12). Ideally, the chest piece 12 is approximately thirty inches (30") long and approximately eight inches (8") to ten inches (10") wide. Alternatively, the chest piece 12 may be manufactured as a single strip of fabric having different widths along the chest piece 12. Although varying widths of the chest piece 12 are not shown for the halter top configuration 10 of the present invention, FIG. 9 illustrates the varying widths of the chest piece 112 of the present invention configured as a bandeau or tube top 100.

Figures 10, 11:
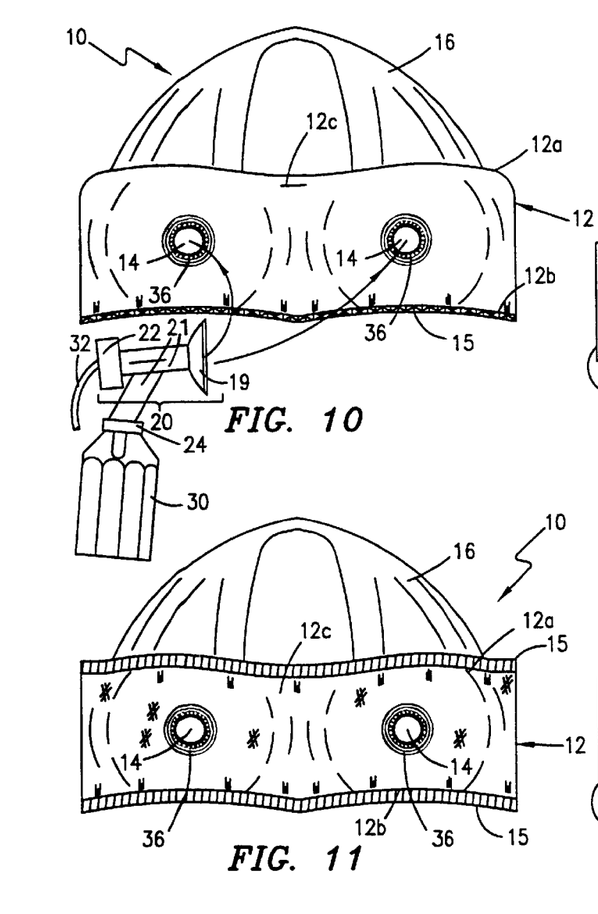
FIG. 10 is a front view of the apparatus of FIG. 1, illustrating the reinforced edges around the openings in the chest piece and elastic ribbing on the bottom edge of the chest piece and the suction device, tubes and bottles ready for positioning.
FIG. 11 is a front view of the apparatus of the present invention configured as a halter top, illustrating the chest piece manufactured from a woven, non-stretchable fabric and elastic ribbing around the openings in, and along the bottom and top edges of, the chest piece.

The chest piece 12 may be manufactured of a stretchable, non-woven material (FIG. 1) or a non-stretchable, woven material (FIG. 11). Suitable stretchable materials include cotton Lycra,® spandex, stretchable terry cloth or similar non-woven fabrics. In the preferred embodiment, cotton Lycra® is used to manufacture the chest piece 12. Alternatively, non-stretchable material may be used to construct the chest piece 12. Suitable non-stretchable materials include woven fabrics such as broadcloth, oxford cloth, muslin, light-weight terry cloth, or synthetic blends such as woven rayon or polyester.

Figure 1:
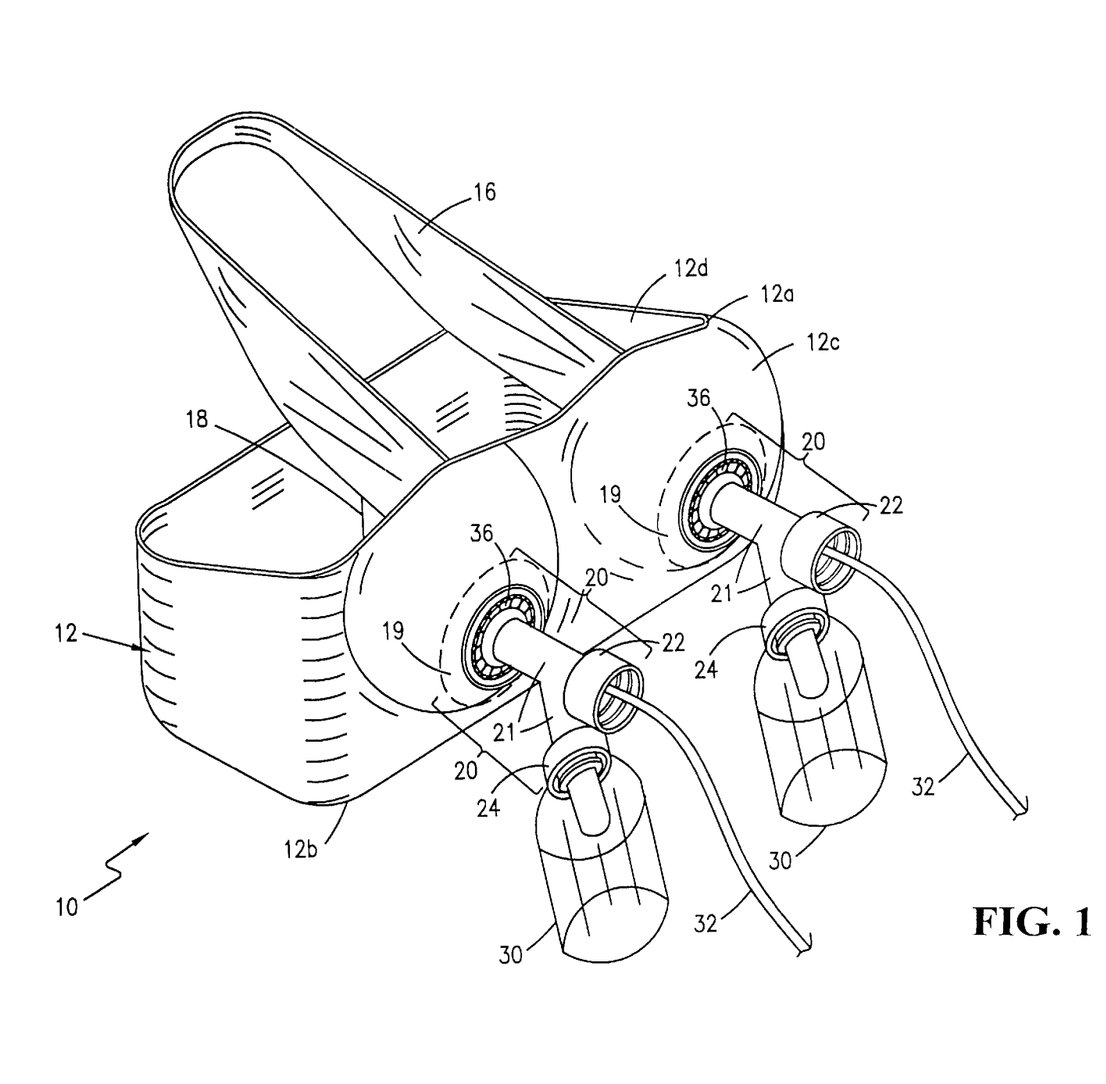
FIG. 1 is a perspective view of the apparatus of the present invention configured as a halter top, illustrating the suction devices from the breast pump in proper placement for milk extraction, and the bottles and tubes connected to the breast pump (not shown)
Figure 12:
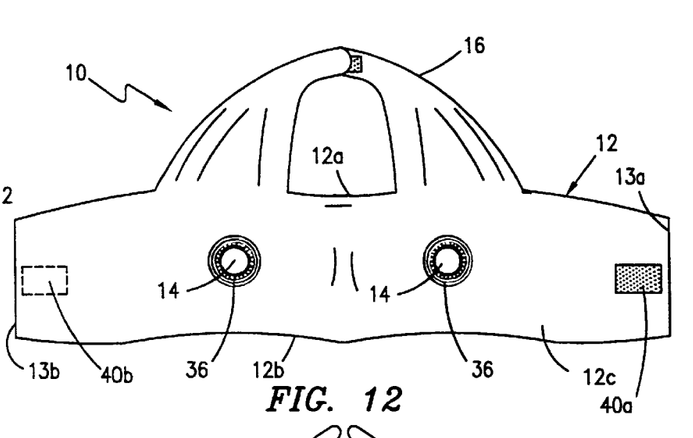
FIG. 12 is a front view of the apparatus of the present invention configured as a halter top, showing the chest piece and neck strap constructed as a single piece and Velcro® closures on the chest piece and neck strap for adjusting the fit of the apparatus around the mother's chest and neck.
Figure 13:
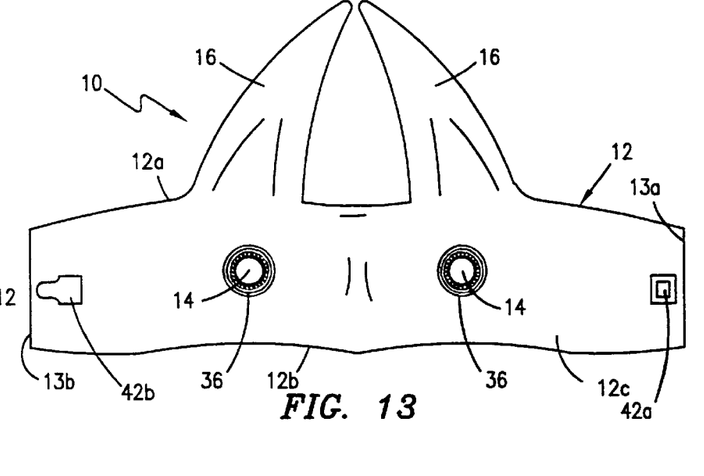
FIG. 13 is a front view of the apparatus of the present invention configured as a halter top, illustrating the chest piece and neck strap constructed as a single piece and the two ends of the neck strap configured for tying around the mother's neck.

During use of the apparatus, the chest piece 12 is wrapped around the nursing mother's chest. The chest piece 12 may be constructed as a single strip of fabric having a first end 13a and a second end 13b (FIGS. 12 and 13). The first end 13a and second end 13b of the chest piece 12 may be permanently secured to each other, thereby creating a single, tubular-shaped chest piece 12 (FIG. 1). Any means known in the art to permanently connect multiple pieces of fabric, such as a needle and thread, a heat-activated fusible material, or a fabric adhesive such as glue may be used to permanently secure the first end 13a and second end 13b of the chest piece 12 together to create the tubular shape of the chest piece 12. The secured ends of the chest piece 12 create a seam 18 in the chest piece 12. In the embodiment of the present invention illustrated in FIG. 1, seam 18 is oriented vertically on the nursing mother's back. The seam 18 may also be located in other positions on the back surface of the chest piece 12, such as angled (not shown). In such case, the first end 13a and the second end 13b of the chest piece 12 would also be angled or slanted in an appropriate direction. If the fabric used to construct the apparatus is tubular in nature at the start of construction, seam 18 would be unnecessary and therefore absent (not shown) from FIG. 1.

Alternatively, the chest piece 12 may be wrapped around the nursing mother's chest as a single strip of fabric having two ends that are temporarily secured to each other (FIG. 12). The first end 13a and the second end 13b of the chest piece 12 may be temporarily secured to each other using connection or fastener means known in the art. Suitable fastener means include VELCRO® hook and loop fastener closures, buttons and button holes, hook and eye closures, snaps or fabric extensions that can be tied. If temporary securing of the chest piece 12 is desired, one component of the closure means, e.g., hook (42b in FIG. 13) is secured to the first end 13a of the chest piece 12 and the complementary component of the closure means, e.g., eye (42a in FIG. 13) is secured to the second end 13b of the chest piece 12.

Figure 8:
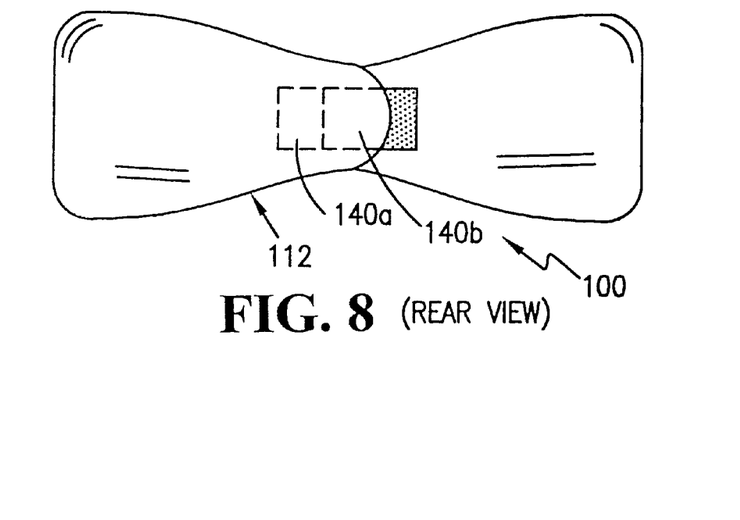
FIG. 8 is a rear view of the apparatus of FIG. 2, with the chest piece having a varied width along the back and showing VELCRO® hook loop fastener closures on the ends of the chest piece.

When the chest piece 12 is wrapped around the nursing mother's chest, the components of the closure means are engaged or mated to temporarily fasten the first end 13a and the second end 13b of the chest piece 12 together. The closure means in the halter top configuration 10 of the present invention are not shown in their mated position in FIG. 12. However, FIGS. 8 and 9 show closure means, such as button 141a and button hole 141b (FIG. 9) and VEL-CRO® hook and loop fastener strips 140a and 140b (FIG. 8) in the in their mated positions in the bandeau configuration 100 of the present invention. When the mother has concluded the milk extraction procedure, the components of the closure means are disengaged, freeing the first end 13a and the second end 13b of the chest piece 12. In conjunction with subsequent milk extraction procedures, the steps described above are repeated.

With the embodiments of the present invention having permanent or temporary fastening of the first end 13a and second end 13b of the chest piece 12, the chest piece 12 must fit snugly and continuously around the nursing mother's chest. A secure, tight fit of the chest piece 12 around the mother's chest holds the milk intake component 19 of the suction devices 20 snugly against the nipples of the mother's breasts and prevents leakage around the milk intake component 19 of the suction devices 20. The chest piece 12 does not provide support for the breasts. Instead, chest piece 12 provides support for the suction devices 20.

A nursing mother often notices significant changes (increases and/or decreases) in her chest or brassiere cup size between the first month of her pregnancy and the last month of breast-feeding. The chest piece 12 is not required to be constructed to fit a particular brassiere chest or cup size. However, the chest piece 12 can be constructed as "one size" in that it adjusts to snugly fit the nursing mother during the increases and decreases in her chest or brassiere cup size during pregnancy and breast-feeding. Ideally, the chest piece 12 is constructed in generally accepted industry sizes (e.g., small, medium and large) to accommodate nursing mothers having various chest and cup sizes. In addition, the chest piece 12 may be manufactured to custom fit a particular torso size, if desired.

If the chest piece 12 is constructed of a woven, non-stretchable fabric (FIG. 11), a strip of supporting fabric 15 should be permanently secured to the bottom edge 12b (FIG. 10) and/or the top edge 12a (FIG. 11) of the chest piece 12 using appropriate attachment means. Suitable fabrics for the support strip(s) 15 include elastic and material used in the ribbing around the collar of a t-shirt or sweatshirt. Suitable attachment means include needle and thread, a heat-activated fusible material or a fabric adhesive such as glue. The support strips 15 aid in holding the chest piece 12 snugly to the nursing mother's chest under her breasts.

A neck strap 16 may be included in the apparatus of the present invention, if desired. The neck strap 16 may be constructed of the same fabric used in constructing the chest piece 12. If the optional neck strap is included, it is preferred that the neck strap 16 be manufactured of a stretchable, elastic material. Alternatively, the neck strap 16 may be constructed of ribbon, elastic or a shirred fabric (i.e., fabric which is drawn up with elastic thread).

Figure 3:
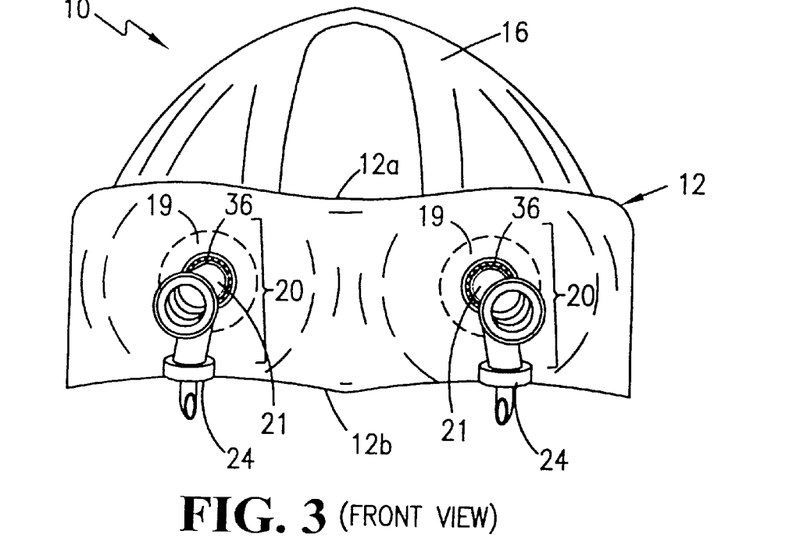
FIG. 3 is a front view of the apparatus of FIG. 1, showing the suction devices in place.
Figure 4:
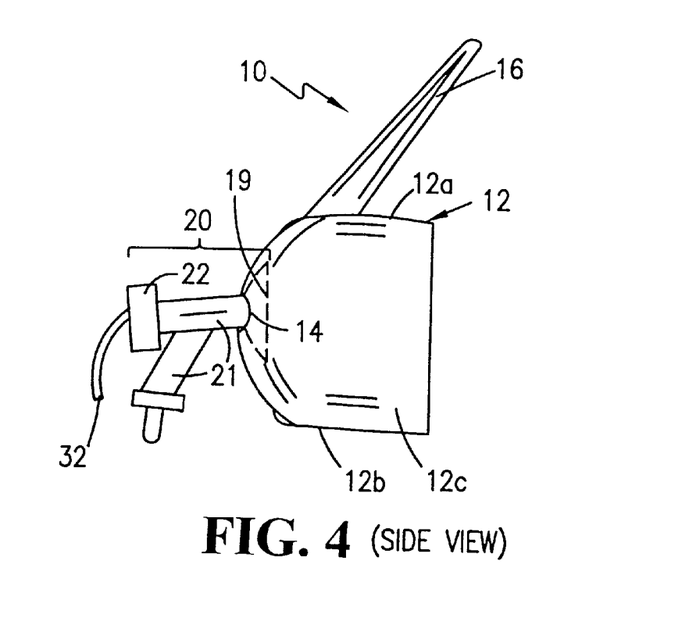
FIG. 4 is a side view of the apparatus of FIG. 1, with the suction device and one tube in place.
Figure 5:
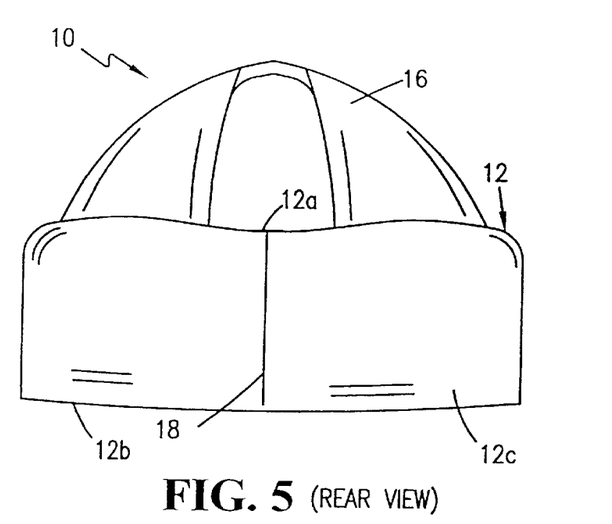
FIG. 5 is a rear view of the apparatus of FIG. 1, showing the chest piece having the same width throughout.
Figure 6:
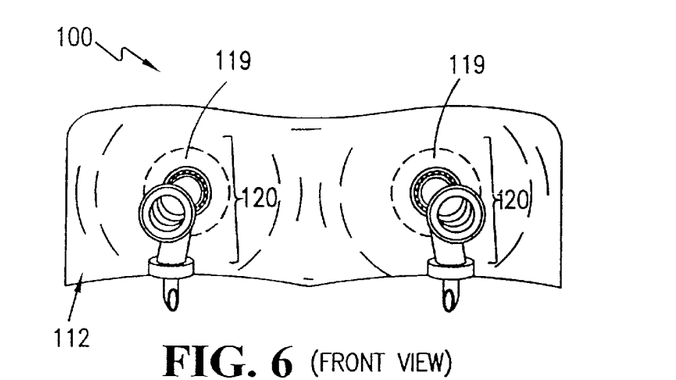
FIG. 6 is a front view of the apparatus of FIG. 2, with the suction devices in place.
Figure 7:
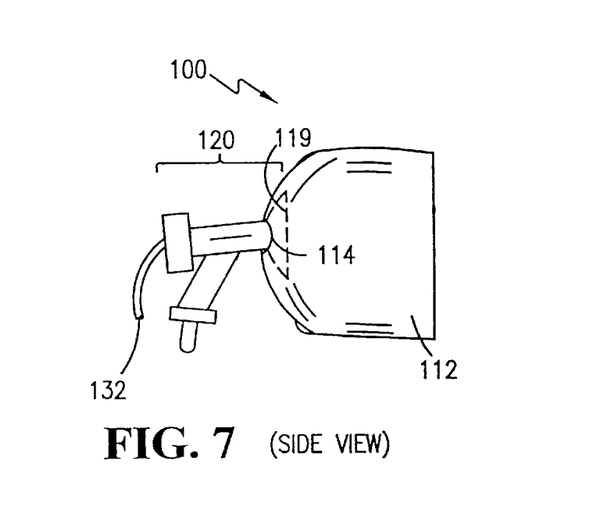
FIG. 7 is a side view of the apparatus of FIG. 2, with the suction device and one tube in place.

The neck strap 16 may have the same width (FIG. 1) or have varying widths (FIGS. 3 and 13). For example, the neck strap 16 of FIG. 13 tapers or decreases in width. In the halter top configuration 10 of the present invention, the neck strap 16 is approximately eighteen inches (18") long when fastened or constructed as one continuous piece and approximately two and one-half to three inches (2½"–3") wide. When two separate pieces are used to create the neck strap 16, each piece should be approximately twelve to fourteen inches (12"–14") long and approximately two and one-half to three inches (2½"–3") wide. The neck strap 16 must be able to stretch to approximately twenty-two inches (22"). Those skilled in the art will understand that these measurements assume that there is some stretch or "give" in the fabric.

The neck strap 16 may be constructed as a single pieces of fabric (FIG. 1) or as two separate pieces of fabric (FIG. 13). Neck strap 16, whether a single piece or two separate pieces, may also be permanently or temporarily secured to the chest piece 12. If the neck strap 16 is constructed as a single piece of fabric having a first end and a second end (FIG. 1), the first end, second end or both ends of the neck strap 16 may be permanently attached to the chest piece 12 using attachment means known in the art. Suitable attachment means include a needle and thread, a fabric adhesive, a fusible bonding material or other similar attachment means.

If the first end of the neck strap 16 is permanently secured to the chest piece 12, the second end may be temporarily or permanently secured to the chest piece 12. The neck strap 16 may be secured to the outer surface 12c of the chest piece 12 or to the inner surface 12d of the chest piece 12 (FIG. 1). Ideally, the neck strap 16 is attached to the inner surface 12d of the chest piece 12 near the top edge 12a of the chest piece 12. The inner surface 12d of the chest piece 12 lies against the nursing mother's skin. The neck strap 16 may also be secured to the inner surface 12d of the chest piece 12 in a different location (not shown), if desired. The neck strap 16 may also be attached to the outer surface 12c of the chest piece 12.

The neck strap 16 may also be constructed as a continuation of the chest piece 12, as in the case of a single knit piece. This is similar to the manner in which a sweater may consist of one knitted piece of clothing. FIG. 13 illustrates the continuous nature of the chest piece 12 and neck strap 16. In FIG. 13, the chest piece 12 and neck strap 16, while continuous with each other, are not permanently secured individually. Thus, in preparing to begin the milk extraction procedure, the nursing mother may temporarily secure the first end 13a and the second end 13b of the chest piece 12 to each other with suitable attachment means. Similarly, the mother may tie or otherwise temporarily secure the first end and the second end of the neck strap 16 to each other.

The neck strap 16 itself may be one continuous piece similar to the neck strap shown in FIG. 1, or it may consist of two pieces (FIGS. 12 and 13). In either case, the neck strap 16 may be continuous with the chest piece 12. The single chest/neck piece 12/16 may be tubular in nature, that is, permanently secured (not shown). Alternatively, the chest/neck piece 12/16 may be temporarily secured, while still continuous as a whole, as illustrated in FIG. 13.

To use the embodiment of the present invention where the chest piece 12 and neck strap 16 are a continuous, permanent piece (FIGS. 12 and 13) and the neck strap 16 is a single strip (FIG. 1), the chest piece 12 and neck strap 16 are placed over the nursing mother's head. The chest piece 12 is positioned around the mother's chest and the neck strap 16 is placed around the mother's neck.

Alternatively, the chest piece 12 and neck strap 16 may comprise a single, continuous piece (FIGS. 12 and 13), with the two ends of the chest piece 12 permanently secured to each other (FIG. 5), and the neck strap 16 itself as two separate strips of fabric (FIG. 13). To use this embodiment of the present invention, the chest piece 12 is placed over the mother's head and positioned around her chest. Thereafter, the two strips comprising the neck strap 16 are temporarily secured to each other around the mother's neck.

Alternatively, the chest piece 12 and neck strap 16 may comprise a single, continuous piece (FIGS. 12 and 13), the two ends of the chest piece 12 temporarily attach to each other (FIG. 2) and the neck strap 16 is two separate pieces of fabric (FIG. 13). With this embodiment, the chest piece 12 is placed around the mother's chest and the two ends thereof temporarily secured to each other. The two pieces of the neck strap 16 are positioned behind the mother's neck, adjusted to fit comfortably and then temporarily secured to one another. It will be appreciated by one skilled in the art that there are numerous variations of the present invention, in addition to the embodiments described above.

If the first end and the second end of the neck strap 16 are attached to the chest piece 12, both ends of the neck strap 16 may be attached to the chest piece 12 on the front portion of the outer surface 12c of the chest piece 12. Ideally, the first end and second end of the neck strap 16 should be evenly spaced apart on the front of the chest piece 12. The first end and the second end of the neck strap 16 should be positioned near the top edge of the chest piece 12 above two openings 14 formed in the chest piece 12. However, the first end and the second end of the neck strap 16 may be attached at any location along the front of the chest piece 12 that will secure the fit of the neck strap 16 around the nursing mother's neck and not interfere with the openings 14 in the chest piece 12.

For example, the first end and the second end of the neck strap 16 may be attached to the top edge of the chest piece 12 (not shown). Alternatively, the first end and the second end of the neck strap 16 may be attached to the chest piece on the inside surface 12d of the chest piece 12 (see FIG. 1). This variation may be desirable where the specific chest or cup size of the mother is known or where the apparatus is constructed as a custom-fit garment.

To use the apparatus configured as a halter top 10, the mother places the chest piece 12 over her head and around her chest. Thereafter, she adjusts the fit of the chest piece 12, if necessary, at the point of closure in the back. The mother places the neck strap 16 over her head and adjusts the fit of the neck strap 16, as necessary.

If desired, the first end only of the neck strap 16 may be permanently secured to the chest piece 12. In this variation, the first end of the neck strap 16 is permanently attached to the chest piece 12 using attachment means identified above with respect to permanent attachment of the first end and the second end of the neck strap 16. The second end of the neck strap 16, however, is removably attached to the chest piece 12 using the temporary closure means described above, such as VELCRO® hook and loop fastener strips. The temporary attachment means are secured to the appropriate location of the chest piece 12 and the neck strap 16. For example, one component of the attachment means (e.g., button) may be secured to the inner surface of the chest piece 12 whereas the corresponding component of the attachment means (e.g., button hole) would be secured to the second end of the neck strap 16.

To use the apparatus of the present invention configured as a halter top 10, the mother places the chest piece 12 over her head and around her chest. The first end of the neck strap 16 is attached to the chest piece 12. Thereafter, she drapes the second end of the neck strap 16 around her neck and secures the second end of the neck strap 16 to the chest piece 12.

If the neck strap 16 is constructed as two separate strips of fabric, each strip has a first end and a second end. In this case, the first end of the first strip is permanently secured to the chest piece 12 as described above. Similarly, the first end of the second strip is permanently attached to the chest piece 12 at a similar location. During use, the second end of the first strip and the second end of the second strip may be temporarily secured around the nursing mother's neck. The second ends of the first and second strips, respectively, may be tied or otherwise secured to each other. The fit of the neck strap 16 around the mother's neck may be adjusted using the second ends of the first and second strips, e.g., by tying the second ends more tightly to each other. A button, snaps or hooks and eyes may be used to fasten the strips to the chest piece 12.

Two openings 14 are formed in the chest piece 12. The openings 14 may be cut in the chest piece 12 using standard cutting means known in the art, such as scissors. The openings 14 are positioned in the chest piece 12 over the locations of the underlying nipples of the mother's breasts. Ideally, the openings 14 are circular, however, various shapes (not shown) such as square or triangular, may be substituted for the circular shape of the openings 14. Any shape may be used for the openings 14 as long as each opening 14 is capable of receiving and fitting snugly around the milk intake component 19 of the suction devices 20.

Each opening 14 must be able to fit snugly around the milk intake component 19 of the suction device 20, but also stretch enough for the milk intake component 19 to fit inside the opening 14. When the apparatus of the present invention is constructed of a stretchable fabric, an opening 14 that is approximately one and one-half inches (1½") in diameter is suitable.

If the chest piece 12 is constructed of stretchable material, the openings 14 do not require any reinforcement or "finishing." However, each opening 14 may be reinforced or finished, if desired. Suitable fabrics for reinforcing or finishing the openings 14 in the chest piece 12 include stretchable fabric used in manufacturing t-shirts or fabric used to construct sweatshirt ribbing. Elastic that is approximately one-fourth to three-eighths inches (¼"–⅜") wide is suitable. Ideally, lingerie elastic is used for this purpose.

When the apparatus of the present invention is constructed of a woven, non-stretchable fabric, each opening 14 must be larger. In particular, each opening 14 should be approximately two and one-half to three inches (2½–3") in diameter. In addition, each opening 14 must be reinforced or finished off with a stretchable fabric or wide elastic. An elastic having an O-shape "cuff" 36 must be added to the edge of the chest piece 12 around each opening 14. Suitable materials for the cuff 36 include elastic or stretchable t-shirt fabric or sweatshirt ribbing such as fabric used to construct the collar of a t-shirt or sweatshirt.

The finishing or ribbing material used to construct the cuff 36 should have elastic properties. Specifically, the cuff 36 must be stretchable enough around each opening 14 so that the milk intake component 19 of the suction device 20 fits through each opening 14 during insertion or removal. But the cuff 36 must be tight enough around each opening 14 so that the milk intake component 19 of the suction device 20 is held against the nipple and prevented from slipping out of the opening 14 thereafter.

To permanently reinforce or finish off the openings 14, a strip of the desired fabric is connected to the chest piece 12 surrounding each opening 14. The reinforcement means are secured or otherwise attached to the chest piece 12 using attachment means known in the art, such as a needle and thread.

Each suction device 20 includes several components, including a milk intake component 19, a cylinder 21 and caps 22 and 24. At the beginning the milk extraction procedure, the milk intake component 19 of the suction device 20 is inserted through an opening 14 in the chest piece 12. The milk intake component 19 of the suction device 20 fits snugly over the nipple of the mother's breast during milk extraction. A cylinder 21 connects to milk intake component 19. Caps 22 and 24 are positioned on the end of each cylinder 21. A tube 32 is inserted into cap 22 of the cylinder 21. Tube 32 also connects to the breast pump. A storage bottle 30 is removably attached to cap 24 of the suction device 20.

Figure 2:
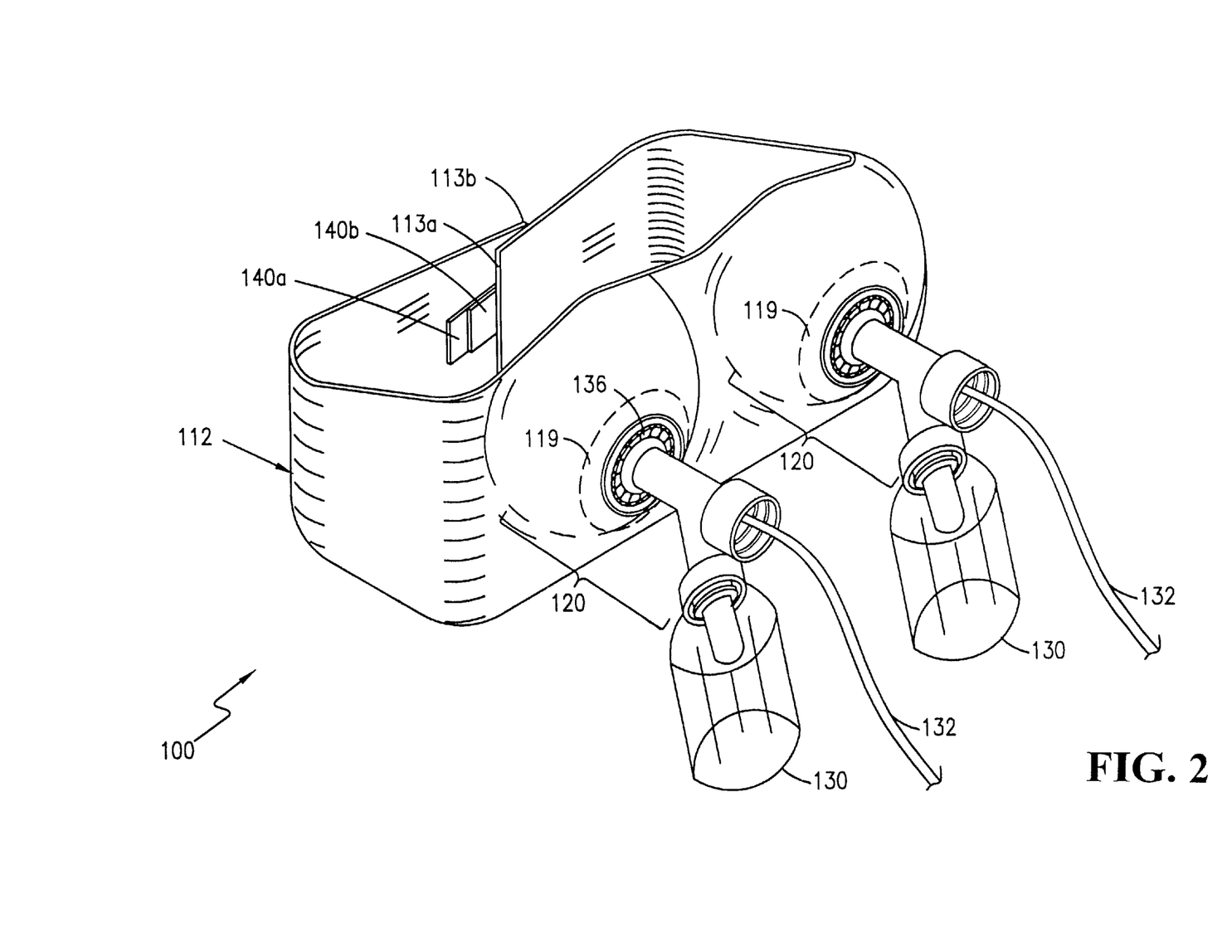
FIG. 2 is a perspective view of the apparatus of the present invention configured as a bandeau or tube top, illustrating the suction devices from the breast pump in place, and the bottles and tubes connected to the breast pump (not shown)

FIGS. 2, 6, 7, 8 and 9 show the preferred embodiment of the apparatus of the present invention wherein the apparatus is configured as a bandeau or tube top 100. The neck strap present in the halter top configuration 10 is omitted in the preferred embodiment 100. The chest piece 112 is constructed of the same fabric used to construct the chest piece 12 of the halter top configuration 10. As illustrated in FIG. 2, the first end 113a and the second end 113b of the chest piece 112 may overlap to temporarily secure the chest piece 112 around the mother's chest. The rear views of the apparatus of the present invention configured as a tube top 110 and configured as a halter top 10 (FIG. 5) may appear to be somewhat similar. That is, the seam 18 evidencing the permanent connection of the first end 13a and the second end 13b of the chest piece 12 in the halter top configuration 10 will appear similar to the line evidencing the temporary connection of the first end 113a and the second end 113b of the chest piece 112 in the tube top configuration 100.

Two openings 114 are formed in the chest piece 112 into which the milk intake components 119 of the suction devices 120 are inserted. The openings 114 may be reinforced or finished off, as desired. As in the halter top configuration 10, tubes 132 and bottles 130 connect to the breast pump (not shown) during the milk extraction procedure.

There are numerous advantages to the apparatus of the present invention. For example, the apparatus holds the milk intake component of the suction device securely to each breast so that the mother's hands are free to do other things. In addition, the apparatus is large enough to provide coverage to the breast area so that it isn't as exposed as when the nursing mother uses other milk extraction devices. In addition, the apparatus of the present invention may be constructed as a "one size" device that can be used by a nursing mother from the first month of her pregnancy through her last month of breast-feeding. The apparatus of the present invention can also be constructed in generally accepted sizes so that nursing mothers having various chest or brassiere cup sizes may use the apparatus. In addition, the apparatus may be constructed for a custom fit to a particular user. Finally, the apparatus is inexpensive to manufacture so that a nursing mother does not have to spend a prohibitive amount of money acquiring a device that she will use for a short time.

Although preferred and alternative embodiments of the present invention have been illustrated in the accompanying Drawings and described in the foregoing Detailed Description of the Invention, it will be understood by those skilled in the art that the invention is not limited to the embodiments disclosed, but is capable of numerous modifications, rearrangements and substitutions of the component parts and elements without departing from the spirit of the invention.

What is claimed is:

1. An apparatus for securing two milk intake components of a suction device to the nipples of a nursing mother's breasts, comprising:
   an elongated elastic chest piece for positioning around the nursing mother's chest, said elongated elastic chest piece having a top edge and a bottom edge, and a first end and a second end;
   two permanently uncovered openings formed in said elongated elastic chest piece for receiving and holding the milk intake components of said suction device therethrough; and
   said elongated elastic chest piece being constructed and arranged to fit snugly around the mother's chest and breasts and accommodate changes in breast size without providing support for the nursing mother's breasts.

2. The apparatus of claim 1 further including a strip of fabric permanently attached to said bottom edge of said chest piece.

3. The apparatus of claim 1 further including closure means permanently attached to said first end and said chest piece.

4. The apparatus of claim 1 further including a neck strap attached to said chest piece, wherein said neck strap has a first end and a second end.

5. The apparatus of claim 4 wherein said first end and said second end of said neck strap are permanently attached to said chest piece.

6. The apparatus of claim 4 wherein said first end of said neck strap is permanently attached to said chest piece and said second end of said neck strap is temporarily attached to said chest piece.

7. The apparatus of claim 4 wherein said first end and said second end of said neck strap are temporarily attached to said chest piece.

8. The apparatus of claim 4 further including closure means secured to said first end and said second end of said neck strap.

9. The apparatus of claim 4 wherein said neck strap is integrally mounted to said chest piece.

10. The apparatus of claim 1 further including two straps permanently attached to said top edge of said chest piece, said two straps capable of being temporarily attached to each other behind the nursing mother's neck.

11. The apparatus of claim 1 further including two fabric strips attached to said chest piece, wherein one of said two fabric strips surrounds each opening formed in said chest piece.

12. The apparatus of claim 11 wherein each of said two fabric strips is O-shaped.

13. The apparatus of claim 11 where each of said two fabric strips has elastic properties.

14. An apparatus for securing two milk intake components of a suction device to the nipples of a nursing mother's breasts, comprising:

an elongated elastic chest piece for positioning around the nursing mother's chest, said elongated elastic chest piece having a top edge and a bottom edge, and a first end and a second end;

said elongated elastic chest piece being constructed and arranged to fit snugly around the mother's chest and breasts and accommodate changes in breast size without providing support for the nursing mother's breasts;

a strip of fabric permanently secured to the bottom edge of said elongated elastic chest piece;

two permanently uncovered openings formed in said elongated elastic chest piece for receiving and holding the milk intake components of said suction device;

two O-shaped fabric strips secured to said elongated elastic chest piece, one of the O-shaped strips located around each opening formed in said elongated elastic chest piece;

closure means secured to said elongated elastic chest piece for adjusting the fit of said elongated elastic chest piece around the nursing mother's chest;

a neck strap affixed to said elongated elastic chest piece; and closure means attached to said neck strap and to said elongated elastic chest piece to adjust the fit of said neck strap around the nursing mother's neck.

15. The apparatus of claim 14 wherein said fabric strip secured to said bottom edge of said chest piece has elastic properties.

16. An apparatus for securing two milk intake components of a suction device to the nipples of a nursing mother's breasts, comprising:

an elongated elastic chest piece for positioning around the nursing mother's chest, said elongated elastic chest piece having a top edge and a bottom edge, and a first end and a second end, and an inner surface and an outer surface;

said elongated elastic chest piece being constructed and arranged to fit snugly around the mother's chest and breasts and accommodate changes in breast size without providing support for the nursing mother's breasts;

two strips of fabric permanently secured to said elongated elastic chest piece, one of the strips permanently secured to said bottom edge of said elongated elastic chest piece, and the other one of the strips permanently secured to said top edge of said elongated elastic chest piece;

two permanently uncovered openings formed in said elongated elastic chest piece for receiving and holding the milk intake components of said suction device;

two O-shaped strips secured to said elongated elastic chest piece, one of the O-shaped strips located around each opening formed in said elongated elastic chest piece;

closure means secured to said elongated elastic chest piece for adjusting the fit of said elongated elastic chest piece around the nursing mother's chest;

a neck strip affixed to said elongated elastic chest piece near said top edge of said elongated elastic chest piece; and closure means attached to said neck strap and to said elongated elastic chest piece to adjust the fit of said neck strap around the nursing mother's neck.

17. The apparatus of claim 16 wherein said strips secured to said bottom edge and top edge of said chest piece have elastic properties.

18. The apparatus of claim 16 wherein said neck strap is affixed to the outer surface of said chest piece.

19. The apparatus of claim 16 wherein said neck strap is affixed to the inner surface of said chest piece.

20. The apparatus of claim 16 wherein each of said two O-shaped strips has elastic properties.

\* \* \* \* \*

UNITED STATES PATENT AND TRADEMARK OFFICE
CERTIFICATE OF CORRECTION

PATENT NO. : 6,004,186
DATED : December 21, 1999
INVENTOR(S) : Penny

It is certified that error appears in the above-identified patent and that said Letters Patent is hereby corrected as shown below:

<u>Title page,</u>
Item [22], PCT Filed, please delete "Jun. 30, 1998" and substitute -- Jun. 30, 1997 --.

Signed and Sealed this

Twenty-first Day of June, 2005

JON W. DUDAS
*Director of the United States Patent and Trademark Office*